(12) United States Patent
Schmitt et al.

(10) Patent No.: US 8,728,556 B2
(45) Date of Patent: May 20, 2014

(54) HYDROLYSED PROTEIN-POLYSACCHARIDE COMPLEXES

(75) Inventors: Christophe Joseph Etienne Schmitt, Servion (CH); Sandra Isabel Laneuville Ballester, Quebec (CA); Sylvie Turgeon, Quebec (CA); Sylvie Gauthier, Quebec (CA)

(73) Assignee: Nestec S.A., Vevey (CH)

( * ) Notice: Subject to any disclaimer, the term of this patent is extended or adjusted under 35 U.S.C. 154(b) by 220 days.

(21) Appl. No.: 13/129,501

(22) PCT Filed: Nov. 30, 2009

(86) PCT No.: PCT/EP2009/066038
§ 371 (c)(1),
(2), (4) Date: Jun. 6, 2011

(87) PCT Pub. No.: WO2010/063669
PCT Pub. Date: Jun. 10, 2010

(65) Prior Publication Data
US 2011/0236554 A1   Sep. 29, 2011

(30) Foreign Application Priority Data
Dec. 4, 2008 (EP) .................................... 08170653

(51) Int. Cl.
*A23C 9/00* (2006.01)
*A23J 1/00* (2006.01)

(52) U.S. Cl.
USPC ................. 426/580; 426/34; 426/42; 426/43; 426/44; 426/46; 426/47; 426/48; 426/49; 426/52; 426/656; 426/657; 426/658

(58) Field of Classification Search
USPC ........... 426/34, 42, 43, 44, 46, 47, 48, 49, 52, 426/580, 656, 657, 658
See application file for complete search history.

(56) References Cited

U.S. PATENT DOCUMENTS

| 3,944,680 | A |   | 3/1976 | van Pelt et al. |
| 5,342,643 | A | * | 8/1994 | Wolf et al. .................... 426/590 |
| 6,197,319 | B1 |   | 3/2001 | Wang et al. |
| 6,858,405 | B1 |   | 2/2005 | Nakamura et al. |

FOREIGN PATENT DOCUMENTS

| EP | 0 340 035 | 11/1989 |
| GB | 2 370 751 | 7/2002 |

OTHER PUBLICATIONS

Connolly et al.; "Effect of a Proteinase on the Macromolecular Distribution of Acacia senegal Gum", Carbohydrate Polymers 8 (1988) pp. 23-32.
Samant et al.,; "Protein-polysaccharide interactions: a new approach in food formulations", International Journal of Food Science and Technology (1993) 28, pp. 547-562 XP008014427.
Benichou et al.; "Double emulsions stabilized with hybrids of natural polymers for entrapment and slow release of active matters", Advances in Colloid and Interface Science 108-109 (2004) pp. 29-41 XP-002451830.

* cited by examiner

*Primary Examiner* — Leslie Wong
(74) *Attorney, Agent, or Firm* — K&L Gates LLP

(57) ABSTRACT

The present invention relates to hydrolysed protein-polysaccharide complexes, and more specifically to those complexes formed by complex formation of a protein with a polysaccharide followed by hydrolysis. The resulting complexes have good emulsifying and stabilizing properties and can be used in food, cosmetic or pharmaceutical products. The invention further relates to the method of manufacture of such complexes.

17 Claims, 3 Drawing Sheets

| Sample | Enzyme | DH (%) OPA |
|---|---|---|
| Protein-polysaccharide complex | Enzeco fungal protease concentrate[1] | 5.9 ± 0.5 |
| Protein blank | Enzeco fungal protease concentrate[1] | 16.8 ± 1.3 |
| Protein-polysaccharide complex | Acid Protease II[2] | 5.5 ± 0.2 |
| Protein blank | Acid Protease II[2] | 6.6 ± 0.8 |
| Protein-polysaccharide complex | Enzeco Bromelain concentrate[1] | 3.7 ± 0.2 |
| Protein blank | Enzeco Bromelain concentrate[1] | 4.6 ± 0.5 |

1: enzyme commercially obtained from Enzyme Development Corporation (EDC)
2: enzyme commercially obtained from Amano.

Figure 3

HYDROLYSED PROTEIN-POLYSACCHARIDE COMPLEXES

FIELD OF THE INVENTION

The present invention relates to hydrolysed protein-polysaccharide complexes, and more specifically to those obtained by complex formation between a protein and a polysaccharide followed by hydrolysis. The resulting complexes have good emulsifying and stabilising properties and can be used in food, cosmetic or pharmaceutical products. The invention further relates to the method of manufacture of such complexes.

BACKGROUND OF THE INVENTION

Protein-polysaccharide complexes are well known in the art for their ability to stabilise emulsions and foams. For instance, U.S. Pat. No. 3,944,680 describes the use of these complexes as a favoured alternative to globular protein alone in storage stable whippable emulsions.

U.S. Pat. No. 6,197,319 relates to the use of these complexes in cosmetic compositions as a means to avoid unstable products which can be obtained when proteins or polysaccharides are used individually.

The use of a microfragmented ionic polysaccharide/protein complex dispersion as fat substitute in food products such as ice cream, salad dressings, dips, spreads and sauces is described in EP 340 035.

An emulsifier having high emulsifying capacity is described in WO 2004/078334. The emulsifier is produced by complex formation between an acidic polysaccharide and a protein or hydrolysed protein under heat at a pH of 2 to 5.

Further, Pilosof, A. M. R. et al. in Food Hydrocolloids, 19, 2005, 361-369 discuss the effects of hydrolysed sunflower protein on the interaction with polysaccharide in foams. Limited hydrolysis of the protein is seen to enhance its foaming properties and also affect the protein-polysaccharide interactions.

WO2004/028281 discloses the use of an electrostatically bound protein-polysaccharide complex as a surfactant and a stabiliser in any type of emulsions or foams.

OBJECT OF THE INVENTION

It is therefore an object of the invention to further improve the emulsifying and stabilising properties of protein-polysaccharide complexes.

SUMMARY OF THE INVENTION

This object is solved by means of the independent claims. The dependent claims further develop the central idea of the invention.

Thus, in a first aspect, the invention relates to a hydrolysed protein-polysaccharide complex obtained and/or obtainable by hydrolysis of a protein-polysaccharide complex by an enzyme.

The use of a complex according to any of claims 1 to 5 as an emulsifier and/or stabiliser in food products, preferably selected from desserts, frozen desserts, dairy products, pet-food, culinary products, clinical nutrition products; cosmetic products preferably selected from creams, foams, mousses, gels, shampoos, emulsions; or pharmaceutical products preferably selected from tablets, capsules, syrups, also forms part of the invention.

Finally, the invention also concerns a method for the manufacture of a hydrolysed protein-polysaccharide complex comprising the steps of:
a. Mixing a solution of protein with a polysaccharide such as to induce the formation of a complex
b. Hydrolysing the formed complex with an enzyme, preferably to a degree of hydrolysis of the protein in the hydrolysed protein-polysaccharide complex of 1 to 50%, more preferably 2 to 25%, even more preferably 3.5 to 20%, to obtain said hydrolysed protein-polysaccharide complex.

FIGURES

The invention is further illustrated by means of the accompanying figures, wherein FIG. 1 shows RP-HPLC profiles obtained on C18 column for WPI (BiPRO)/acacia gum hydrolyzed complexes or WPI hydrolysate at pH 4.2 by: A) Enzeco fungal protease concentrate; B) Acid Protease II; C) Enzeco Bromelain concentrate. In all samples, enzymes were heat inactivated prior to RP-HPLC analysis and de-complexation.

FIG. 3 is a table summarising the DH values obtained for WPI and WPI/Acacia gum complex hydrolysis (for 2 hours) at pH 4.2 measured by OPA method.

DETAILED DESCRIPTION OF THE INVENTION

Figure 1:
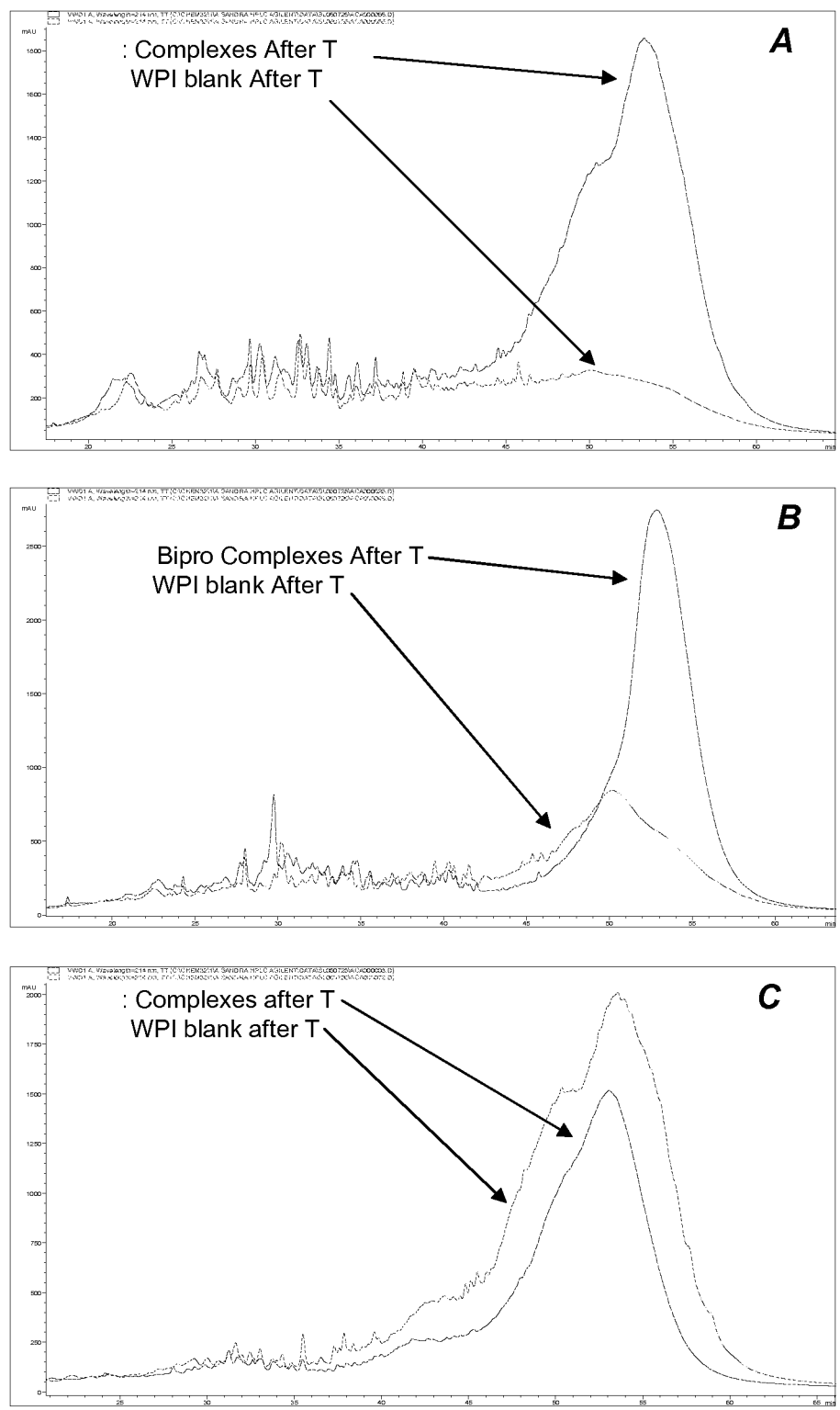

The invention relates to hydrolysed protein-polysaccharide complexes. In the context of the present invention, the term "hydrolysed protein-polysaccharide complex" describes a complex between a protein and a polysaccharide which, after complex formation between the intact protein and the polysaccharide has been subjected to hydrolysis.

By the term "complex" is meant any form of association between the protein and the polysaccharide. Such association may involve hydrophobic interactions, van der Waal interactions, electrostatic interactions, hydrogen-bonding, covalent interactions or dipole-dipole induced interactions.

The complexes of the invention are preferably electrostatically bound complexes. Thus, the protein preferably has an overall net charge opposite to the overall net charge of the polysaccharide. However, electrostatic complexes formed by means of protein charge patches, i.e. in conditions where the protein and the polysaccharide have similar net charge, are also covered by this application.

In the context of the present invention, the term "hydrolysis" refers to the hydrolysis of the protein, once bound to the polysaccharide.

The hydrolysis is preferably carried out using an enzyme. The enzyme is selected such that it can act on the protein in the protein-polysaccharide complex. Such enzyme may be selected from endoprotease such as pepsin, trypsin, chymotrypsin, α-chymotrypsin, bromelain, papain, ficin, endoprotease from porcine pancreas, bovine pancreas, porcine stomach mucosa, porcine gastric mucosa, porcine stomach linings, *Bacillus subtilis, Bacillus* spp., *Aspergillus oryzae, Aspergillus sojae, Aspergillus* spp., *Rhizopus niveus, Carica papaya, Ananas comosus*, Bromeliceae family, *Ficus* species, exoprotease from *Aspergillus oryzae, Aspergillus sojae, Aspergillus* spp., *Carica papaya*. Preferably, the enzyme is an endoprotease.

Enzymes that may be used in the present invention are commercially available from Novozymes for example under the name of Alcalase®, Neutrase®, Protamex®, Flavourzyme®.

The degree of hydrolysis of the protein in the protein-polysaccharide complex with an enzyme has been shown to be less than the degree of hydrolysis with the same enzyme when the protein is free (cf. FIG. 3). This result is expected as the access to the cleaving site on the protein is somewhat hindered by the presence of the polysaccharide. However, the lower degree of hydrolysis achieved in the protein-polysaccharide complexes has no effect on the performance of the complexes as stabilising agents. Indeed, it has been found that a degree of hydrolysis of 1 to 50%, preferably 2 to 25%, more preferably 3.5 to 20% is suitable in order to achieve the advantageous effects of the invention.

The protein of the protein-polysaccharide complex prior to hydrolysis is preferably selected from one or more of milk, soy, egg, meat, fish or plant protein. Preferably, it is a milk protein such as whey protein or casein, more preferably a bovine milk protein. Even more preferably, it is a bovine whey protein.

The polysaccharide used in the present invention may be any polysaccharide capable of intermolecular association with a protein. Thus, it is preferably an anionic or cationic polysaccharide. Polysaccharide of the invention may be selected from gums, hydrocolloids, microbial or fungal exo-polysaccharides. Preferably it is selected from one or more of acacia gum, pectins, carrageenans, mammalian gelatine such as pork gelatine, fish gelatine, arabinogalactans, rye arabinoxylans, wheat arabinoxylans, alginate, propylene glycol alginate, carboxymethylcellulose, chitosan, xanthan gum, agar, exo-polysaccharides from lactic bacteria. Most preferably the polysaccharide is selected from acacia gum and/or chitosan.

In the complexes of the invention, the degree of hydrolysis of the protein may vary between 1 to 50%. Preferably, it is 2 to 25%, more preferably it is 3.5 to 20%.

The peptide profile resulting from protein hydrolysis within the complex may be determined upon de-complexation of the protein fraction from the polysaccharide. By "de-complexation" is meant disassociation of the protein-polysaccharide complex. De-complexation can be achieved by pH change and polysaccharide precipitation in acetonitrile, for example.

Upon de-complexation, the protein profiles may be analysed, for example by C18 RP-HPLC. This is a method known in the art for peptide profile characterisation. It was found that the protein profiles were different from those of the protein hydrolysed with the same enzyme but in the absence of complex formation with a polysaccharide. This is illustrated in FIG. 1 (A, B and C) which shows that the hydrolysis of the protein with three different enzymes did not occur at the same sites in the proteins associated to a polysaccharide in the form of a complex compared to the proteins which have not been previously associated with a polysaccharide.

Therefore, it can be seen that the complexes obtained by hydrolysis of a protein-polysaccharide complex compared to the complexes formed from association of hydrolysed protein with a polysaccharide differ in structure.

Figure 2:
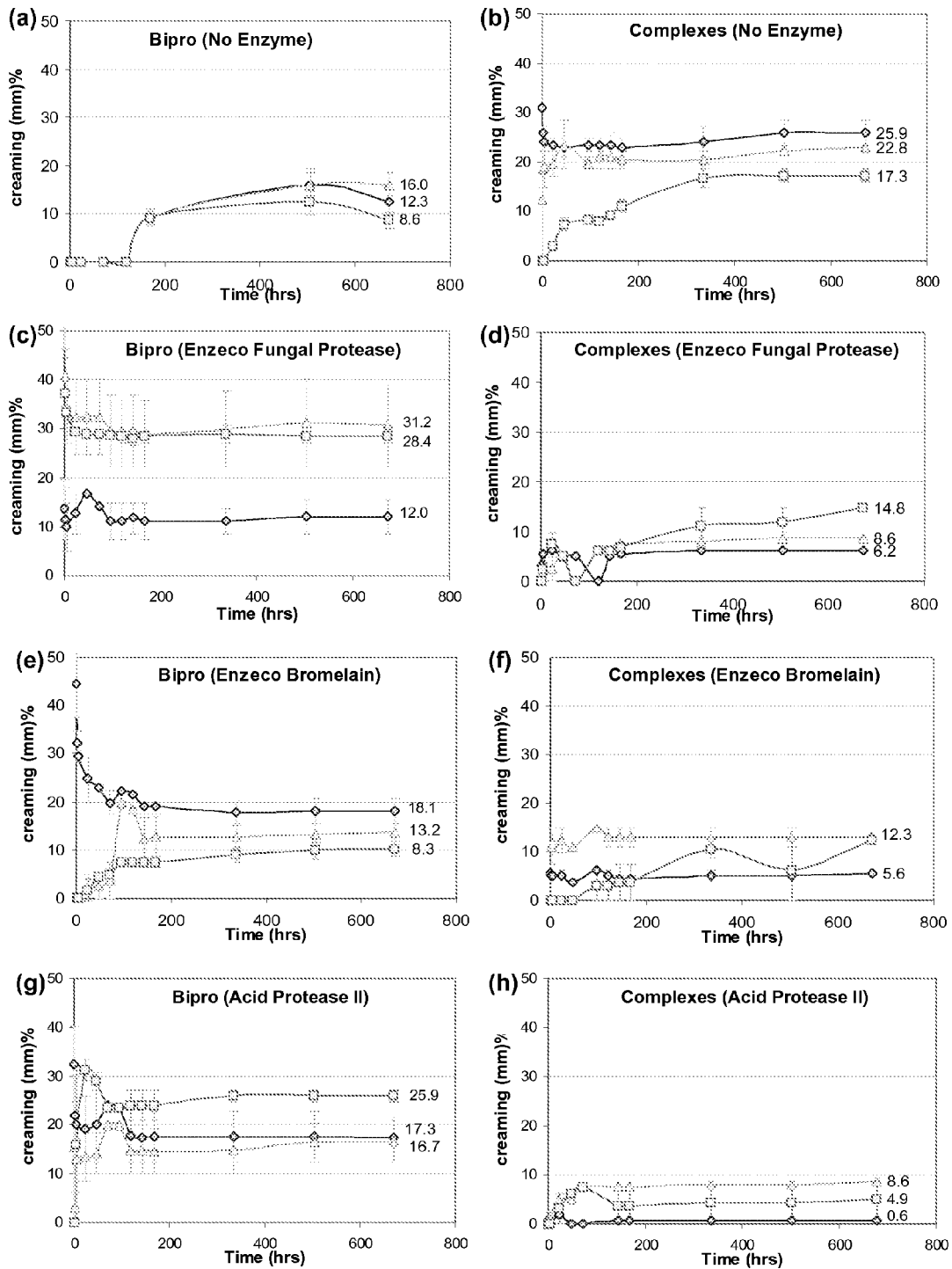
FIG. 2 illustrates the height of the creamed layer (%) measured over time for emulsions prepared with (◇) 0.1 wt %; (△) 0.5 wt % or (▇) 1.0 wt % WPI or WPI/Acacia gum complexes with (a, b) No enzyme; or hydrolysed with (c, d) Enzeco Fungal Protease; (e, f) Enzeco Bromelain; and (g, h) Acid Protease II.

In addition, it was shown that the complexes of the invention provide increased emulsifying stability over time compared to non-hydrolysed complexes, non-hydrolysed protein alone, or hydrolysed protein. This is illustrated in FIG. 2 which shows the best creaming stability over time for complexes which have been hydrolysed by fungal protease, bromelain or acid protease. The hydrolysed protein-polysaccharide complexes obtained by hydrolysis of the complex with acid protease showed particularly good results in terms of creaming stability. In the examples shown in FIG. 2 the fungal protease and the bromelain were obtained commercially from Enzyme Development Corporation. They comprise endoproteases from *Aspergillus oryzae* and endoproteases from the Bromeliceae respectively. The acid protease II was commercially available from Amano and comprises endoproteases from *Rhizopus niveus*.

The complexes of the invention can therefore be used as emulsifiers and/or stabilisers in food, cosmetic or pharmaceutical products.

Food products comprising the complexes of the invention are preferably selected from desserts, frozen desserts, dairy products, petfood, culinary products, clinical nutrition products etc. In particular, they may include sauces, soups, mayonnaises, salad dressings, creams, ice cream, chocolate, mousses, milk, etc.

The complexes of the invention may be used in cosmetic products such as creams, foams, mousses, gels, shampoos, emulsions, etc.

The pharmaceutical products to which the complexes of the invention may be added include tablets, capsules, syrups, etc.

When used as emulsifier and/or stabiliser, the complexes are preferably present in the product in an amount of 0.01 to 10 wt %, preferably 0.1-5 wt %, most preferably 0.1-0.5 wt % of said product. It has indeed been found that the emulsifying and stabilising properties are optimal at low concentrations. The products of the invention thus provide the advantage that they are highly effective emulsifiers and/or stabilisers.

The invention further relates to a method of manufacture of these hydrolysed protein-polysaccharide complexes.

The first step in the method includes the mixing of a solution of protein and polysaccharide such as to induce formation of a complex.

The protein used in the method of the present invention preferably has not been subjected to any hydrolysis step prior to mixing with the polysaccharide.

The protein may be selected from one or more of milk, soy, egg, meat, fish or plant protein. Preferably, it is a milk protein such as whey protein or casein, more preferably a bovine milk protein. Even more preferably, it is a bovine whey protein.

The polysaccharide used in the present invention may be any polysaccharide capable of intermolecular association with a protein. Thus, it is preferably an anionic or cationic polysaccharide. Polysaccahride of the invention may be selected from gums, hydrocolloids, microbial or fungal exo-polysaccharides. Preferably it is selected from one or more of acacia gum, pectins, carrageenans, mammalian gelatine such as pork gelatine, fish gelatine, arabinogalactans, rye arabinoxylans, wheat arabinoxylans, alginate, propylene glycol alginate, carboxymethylcellulose, chitosan, xanthan gum, agar, exo-polysaccharides from lactic bacteria. Most preferably the polysaccharide is selected from acacia gum and/or chitosan.

The conditions for inducing formation of a complex, in particular for inducing formation of an electrostatically bound complex vary depending on the source of protein and of polysaccharide used.

The protein and the polysaccharide may be mixed in a protein:polysaccharide weight ratio of 20:1 to 1:20. Preferably, the protein and the polysaccharide are mixed in a protein:polysaccharide weight ratio of 5:1 to 1:5, more preferably 2:1 to 1:2. Most preferably, the protein and the polysaccharide are mixed in a protein:polysaccharide weight ratio of 2:1.

The amount of polysaccharide in the solution is preferably 0.1 to 10%, more preferably 0.4 to 5%.

In the present invention, it has been found that the pH of the solution may be adjusted such as to induce electrostatic association of the protein with the polysaccharide. The pH of a solution containing the protein and the polysaccharide may vary from 3.0 to 8.0, preferably from 3.0 to 7.0. In a preferred embodiment, the pH may vary from 3.0 to 5.0. In another embodiment, the pH may vary from 6.0 to 7.0.

For instance, when whey proteins are mixed with an anionic polysaccharide such as acacia gum, it is preferred that the pH is between 3.0 and 5.0, more preferably about 4.2.

When whey proteins are mixed with a cationic polysaccharide such as chitosan, it is preferred that the pH is between 6.0 and 7.0, more preferably about 6.5.

The pH adjustment may be made by using conventional acids such as hydrochloric acid, phosphoric acid, citric acid, acetic acid, formic acid or bases such as sodium hydroxide, potassium hydroxide.

The solution is mixed for the amount of time required to induce complex formation between the protein and the polysaccharide. The time may vary from 1 second to 30 minutes. Complex formation may be instantaneous. Complex formation can be evidenced by methods known to the skilled person such as turbidity measurements, light scattering measurements or conductivity measurements.

The intact protein-polysaccharide complexes are then hydrolysed, for example with an enzyme.

The enzyme is selected such that it can act on the protein in the protein-polysaccharide complex. Such enzyme may be selected from endoprotease such as pepsin, trypsin, chymotrypsin, α-chymotrypsin, bromelain, papain, ficin, endoprotease from porcine pancreas, from bovine pancreas, porcine stomach mucosa, porcine gastric mucosa, porcine stomach linings, *Bacillus subtilis*, *Bacillus* spp., *Aspergillus oryzae*, *Aspergillus sojae*, *Aspergillus* spp., *Rhizopus niveus*, *Carica papaya*, *Ananas comosus*, Bromeliceae family, *Ficus* species, exoprotease from *Aspergillus oryzae*, *Aspergillus sojae*, *Aspergillus* spp., *Carica papaya*. Preferably, the enzyme is an endoprotease.

Enzymes that may be used in the present invention are commercially available from Novozymes for example under the name of Alcalase®, Neutrase®, Protamex®, Flavourzyme®.

The protein to enzyme ratio in the solution is 1:5 to 1:1000, preferably 1:10 to 1:100, more preferably 1:50.

The hydrolysis may be carried out at a temperature ranging from 30 to 70° C. The optimal temperature depends on the choice of enzyme. Preferably, the temperature at which the hydrolysis is carried out is between 40 and 50° C.

The hydrolysis may be carried out for 10 minutes to 3 hours, preferably for about 2 hours.

The protein-polysaccharide complex is preferably hydrolysed to a hydrolysis degree of 1 to 50%, more preferably 2 to 25%, even more preferably 3.5 to 20%. The degree of hydrolysis is determined by the OPA (o-phthaldialdehyde) method which is known to a person of skill in the art for following protein hydrolysis.

The resulting hydrolysed protein-polysaccharide complex has the advantage of being highly efficient as an emulsifier and/or stabiliser in compositions to which it is added. Furthermore, it comprises only natural ingredients such that it is more appealing than traditional emulsifiers which consist of chemically modified or synthesised products. Also, the complexes of the invention are versatile in terms of the products they may be included into. For instance, by tuning the choice of protein and polysaccharide, they function as emulsifiers and/or stabilisers over a wide pH range. For instance, they can be used in acidic products having a pH of about 4.5 such as mayonnaise as well as in products having a pH over 6.5 such as milk.

After hydrolysis, it may be advantageous to inactivate the enzyme. Enzyme inactivation may be done by heat treatment, pressure treatment or addition of an inhibitor specific to the enzyme. Preferably, it is carried out by heat treatment of the solution comprising the hydrolysed protein-polysaccharide complex and the enzymes. The heat treatment is preferably carried out at a temperature of 80 to 100° C. for 5-30 minutes.

Additionally, the solution after hydrolysis, and optionally after enzyme inactivation, may be subjected to ultrafiltration. This has the advantage of separating the complexes of the invention from the free peptides generated by the hydrolysis step.

In a preferred embodiment, the solution is then dried by any method known in the art such as spray-drying, freeze-drying or vacuum-drying.

The complexes of the invention can therefore be in the form of a solution, a gel, or a dried powder.

In a further embodiment, the hydrolysed protein-polysaccharide complexes may be dried in the presence of further ingredients. Alternatively, the dried hydrolysed protein-polysaccharide complex may be mixed with other dried ingredients.

The resulting products can be for instance a milk powder or dehydrated soup powder comprising the complexes of the invention.

The present invention is further illustrated by means of the following non-limiting examples.

EXAMPLES

Example 1

Preparation of a Hydrolysed Acacia Gum-Whey Protein Complex

Whey protein isolate (WPI—BiPro from Davisco Foods International) is mixed with acacia gum (Instant gum from Colloides Naturels International) at a protein to polysaccharide weight ratio of 2:1, a total WPI concentration of 2 wt % (protein basis) and the pH was adjusted to 4.2. Enzeco® Bromelain enzyme concentrate was then added to the solution in a ratio of protein to enzyme of 1:50. After 2 hours, the hydrolysis degree was 3.7% and the hydrolysed complex was heat treated (90° C., 15 minutes) to inactivate the enzyme and ultrafiltered to remove the unbound peptides generated by the protease. The resulting hydrolysed protein-polysaccharide complex was freeze dried to give a powder.

Example 2

Preparation of a Hydrolysed Chitosan-Whey Protein Complex

In the present example, chitosan and whey proteins were used as the polysaccharide and protein respectively.

Chitosan 252 (de-acetlyation degree>90%, Mahtani Chitosan PVT Ltd) was obtained from France Chitine. Whey protein isolate was obtained from Davisco Foods International under the tradename of BiPro®.

An aqueous dispersion of chitosan at 50° C. was adjusted to pH 5.9 prior to mixing with the protein. The protein (in an aqueous solution) was then added to the chitosan dispersion and the pH was adjusted to 6.5 with acetic acid.

The whey protein concentration in the mixture was 0.9 wt %. The chitosan concentration in the mixture was 0.45 wt %. After 20 minutes of mixing, a fungal protease from *Bacillus subtilis* (Corolase 7089) was added at a concentration of 0.018 wt %. The mixture was kept at 50° C. under stirring for 2 hours to obtain a hydrolysis degree of 12%.

The mixture was then ultrafiltered at 50° C. using a Prep/Scale Spiral Wound TFF 1 Module PZHK with MWCO of 100 kDa (0.09 m$^2$). Inlet pressure was set to 0.75 bar (speed 6 of the pump).

The mixture was first concentrated 2×, then diafiltration was started by adding 1 diavolume (800 mL) of deionised water.

To denature the enzyme in the retentate a heat treatment of 90° C. for 15 minutes was applied. The retentate was then freeze-dried to give a product according to the invention.

Example 3

The hydrolysed acacia gum-whey protein complex obtained in example 1 was tested for emulsifying capacity at three different concentrations (0.1, 0.5 and 1 wt %).

Emulsions were prepared using Sunflower oil (Merit Selection brand). 10 g of oil were added to 90 g of deionised water. Then 0.1, 0.5 and 1 wt % of hydrolysed complex obtained in example 1 and reconstituted in distilled water were added. Finally, 0.02 wt % NaN$_3$ was added as a preservative. The mixture was pre-homogenised with an Ultra-Turrax (Janke-Kunkel, GmBH) for 30 seconds prior to emulsification.

Emulsification was carried out using an Emulsiflex-C5 homogeniser (Avestin Co., Canada) in two passes, namely ~400 bar (6000 psi) and ~80 bar (1100 psi) at room temperature (23° C.)

The results are shown in FIG. 2. It can be seen that the creaming stability, i.e. the resistance of the emulsions to undergo phase separation, of the complexes of the invention (FIGS. 2d, f, h) was better over 28 days of storage compared to non-hydrolysed whey protein alone (FIG. 2a), compared to non-hydrolysed complexes (FIG. 2b) or compared to hydrolysed whey protein alone (FIGS. 2c, e, g).

Furthermore, the results show that a concentration of the hydrolysed complexes of the invention as low as 0.1 wt % is particularly effective at stabilising the emulsion.

The invention claimed is:

1. Hydrolysed protein-polysaccharide complex obtained by hydrolysis of a protein-polysaccharide complex by an endoprotease, the protein-polysaccharide complex is an electrostatically bound complex, the protein is selected from the group consisting of milk, soy, egg, meat, fish and plant protein and combinations thereof, and a degree of hydrolysis of the protein in the hydrolysed protein-polysaccharide complex is 1 to 50%.

2. Complex according to claim 1, wherein the protein is selected from the group consisting of milk, soy, egg, meat, and fish and plant protein and combinations thereof.

3. Complex according to claim 1, wherein the polysaccharide is selected from the group consisting of gums, hydrocolloids, microbial and fungal exo-polysaccharides.

4. A method of making a food product selected from the group consisting of desserts, frozen desserts, dairy products, petfood, culinary products, and clinical nutrition products comprising the step of using as a hydrolysed protein-polysaccharide a complex obtained by hydrolysis of a protein-polysaccharide complex by an endoprotease, the protein-polysaccharide complex is an electrostatically bound complex the protein selected from the group consisting of milk, soy, egg, meat, fish and plant protein and combinations thereof, and a degree of hydrolysis of the protein in the hydrolysed protein-polysaccharide complex is 1 to 50%.

5. Method according to claim 4, wherein the complex is present in an amount of 0.01 to 10 wt % to the product.

6. Method for the manufacture of a hydrolysed protein-polysaccharide complex comprising the steps of:
    mixing a solution of protein and polysaccharide so as to induce the formation of a protein-polysaccharide complex, the protein selected from the group consisting of milk, soy, egg, meat, fish and plant protein and combinations thereof, and the protein-polysaccharide complex is an electrostatically bound complex; and
    hydrolysing the formed complex with an endoprotese, to a degree of hydrolysis of the protein in the hydrolysed protein-polysaccharide complex of 1 to 50%, to obtain the hydrolysed protein-polysaccharide complex.

7. Method according to claim 6, wherein the mixing is performed at a pH so as to induce electrostatic complex formation between the protein and the polysaccharide.

8. Method according to claim 6, where the pH of the solution is 3.0 to 8.0.

9. Method according to claim 6, wherein the weight ratio of protein to polysaccharide is 20:1 to 1:20.

10. Method according to claim 6, wherein the endoprotease is inactivated after the hydrolysis step.

11. Method according to claim 6, wherein the hydrolysis step is followed by ultrafiltration of the obtained mix.

12. Method according to claim 6, wherein the hydrolysis step is followed by a drying step.

13. Complex according to claim 1, wherein the polysaccharide is selected from the group consisting of acacia gum, pectins, carrageenans, mammalian gelatine, arabinogalactans, rye arabinoxylans, wheat arabinoxylans, alginate, propylene glycol alginate, carboxymethylcellulose, chitosan, xanthan gum, agar, exo-polysaccharides from lactic bacteria, and chitosan.

14. Method for producing a pharmaceutical or cosmetic product comprising the step of using a hydrolysed protein-polysaccharide complex obtained by hydrolysis of a protein-polysaccharide complex by an endoprotease to make the product the protein-polysaccharide complex is an electrostatically bound complex, the protein is selected from the group consisting of milk, soy, egg, meat, fish and plant protein and combinations thereof, and a degree of hydrolysis of the protein in the hydrolysed protein-polysaccharide complex is 1 to 50%.

15. Method according to claim 14, wherein the complex is used in an amount of 0.01 to 10 wt % of the product.

16. Method according to claim 6, wherein the endoprotease is selected from the group consisting of pepsin, trypsin, chymotrypsin, α-chymotrypsin, bromelain, papain, ficin, endoprotease from porcine pancreas, from bovine pancreas, porcine stomach mucosa, porcine gastric mucosa, porcine stomach linings, *Bacillus subtilis*, *Bacillus* spp., *Aspergillus oryzae*, *Aspergillus sojae*, *Aspergillus* spp., *Rhizopus niveus*, *Carica papaya*, *Ananas comosus*, *Bromeliceae family*, *Ficus* species, exoprotease from *Aspergillus oryzae*, *Aspergillus sojae*, *Aspergillus* spp., and *Carica papaya*.

17. Method according to claim 6, wherein the endoprotease is inactivated using a step selected from the group consisting of heat treatment, pressure treatment and addition of an inhibitor specific to the endoprotease.

* * * * *